United States Patent
Morich et al.

(10) Patent No.: US 7,282,914 B2
(45) Date of Patent: Oct. 16, 2007

(54) SPECIFIC ENERGY ABSORPTION RATE MODEL

(75) Inventors: Michael A. Morich, Richmond Heights, OH (US); Paul R. Harvey, Best (NL); Zhiyong Zhai, Cleveland, OH (US); Gordon D. DeMeester, Wickliffe, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 5 days.

(21) Appl. No.: 10/560,870

(22) PCT Filed: Jun. 30, 2004

(86) PCT No.: PCT/IB2004/002175

§ 371 (c)(1),
(2), (4) Date: Dec. 14, 2005

(87) PCT Pub. No.: WO2005/001502

PCT Pub. Date: Jan. 6, 2005

(65) Prior Publication Data

US 2007/0096735 A1 May 3, 2007

Related U.S. Application Data

(60) Provisional application No. 60/484,036, filed on Jun. 30, 2003.

(51) Int. Cl.
*G01V 3/00* (2006.01)

(52) U.S. Cl. ...................... 324/318; 600/410

(58) Field of Classification Search ........... 324/318, 324/322, 307, 309; 600/410
See application file for complete search history.

(56) References Cited

U.S. PATENT DOCUMENTS 6,721,588 B2 * 4/2004 Drobnitzky ................ 600/410
6,759,847 B2 * 7/2004 Brinker et al. ............ 324/309
6,812,698 B1 * 11/2004 Tsukamoto ................ 324/309
6,989,673 B2 * 1/2006 Zhu .......................... 324/318
7,030,615 B2 * 4/2006 Gortler ..................... 324/318
2002/0087066 A1 7/2002 Hellinger .................. 600/410
2002/0161294 A1 10/2002 Drobnitzky ............... 600/410
2003/0080738 A1 5/2003 Brinker et al. ............ 324/309
2003/0098687 A1 5/2003 Arneth et al. ............. 324/309
2003/0098688 A1 5/2003 Brinker et al. ............ 324/309

FOREIGN PATENT DOCUMENTS

| EP | 1 083 439 A2 | 3/2001 |
| JP | 03-284241 | 12/1991 |
| JP | 11-253416 | 9/1999 |

OTHER PUBLICATIONS

Brix, G., et al.; Estimation of heat transfer and temperature rise in partial-body regions during MR Procedures; 2002; Mag. Reson. Imag.; 20:65-76.

(Continued)

*Primary Examiner*—Louis M. Arana

(57) ABSTRACT

An MRI apparatus is provided. The apparatus includes a main magnet for generating a main magnetic field in an examination region, a plurality of gradient coils for generating gradient fields within the main field, an RF transmit coil for transmitting RF signals into the examination region and exciting magnetic resonance in a subject disposed therein in accordance with a plurality of imaging parameters, the transmitted RF signals having a SAR associated therewith, and a SAR processor for maintaining the transmitted RF signals below a prescribed SAR level.

4 Claims, 4 Drawing Sheets

OTHER PUBLICATIONS

Gandhi, O.P., et al.; Specific Absorption Rates and Induced Current Densities for an Anatomy Based Model of the Human; 1999; Mag. Reson. Imag.; 41:816-823.

Schwarz, A.J., et al.; SAR and Tissue Heating with a Clinical 31P MRS Protocol Using Surface Coils, Adiabatic Pulses; 2000; Mag. Reson. Imag.; 44:692-700.

* cited by examiner

SPECIFIC ENERGY ABSORPTION RATE MODEL

CROSS REFERENCE TO RELATED APPLICATIONS

This application claims the benefit of U.S. provisional application Ser. No. 60/484,036 filed Jun. 30, 2003, which is incorporated herein by reference.

The following relates to the diagnostic imaging arts. It particularly relates to a magnetic resonance imaging (MRI) and a method for calculating specific energy absorption rate as a function of location along a subject.

In MRI, a substantially uniform temporally constant main magnetic field is generated within an examination region. The main magnetic field polarizes the nuclear spin system of a subject being imaged within the examination region. Magnetic resonance is excited in dipoles which align with the magnetic field by transmitting radio frequency (RF) excitation signals into the examination region. Specifically, RF pulses transmitted via an RF coil assembly tip the dipoles out of alignment with the main magnetic field and cause a macroscopic magnetic moment vector to precess around an axis parallel to the main magnetic field. The precessing magnetic moment, in turn, generates a corresponding RF magnetic resonance signal as it relaxes and returns to its former state of alignment with the main magnetic field. The RF magnetic resonance signal is received by the RF coil assembly, and from received signals, an image representation is reconstructed for display on a human viewable display.

One of the limiting factors when performing magnetic resonance imaging is the specific energy absorption rate (SAR) in subjects undergoing examination. SAR is quantified as Joules of RF per second per kilogram of body weight (Watts/kg). Because there are prescribed SAR limits under which MRI examinations are performed, SAR is one of the considerations in selecting the RF pulses applied to the subject of the MR protocol.

Because SAR is a limiting factor in MRI, it is desirable to estimate SAR accurately so that imaging protocols can be carried out efficiently. Previous models for SAR are generally limited to relating the RF power required for B1 flip angle calibration, along with RF duty cycle, to estimate head SAR for head transmit coils and the whole body SAR for body transmit coils. The models are fairly simplistic and do not account for changes in head SAR, whole body SAR, partial body SAR, and local SAR as a function of patient position.

A global setting of a single maximum SAR level without considering the difference between body parts can unnecessarily limit the RF duty cycle of a given pulse sequence. While the setting of a SAR limit is for the worst case, higher values can be set differently for some imaging positions such as head, knee, and ankle imaging where RF exposed mass is known to be very limited. In situations where SAR less than allowable advantage can be taken of this SAR information for the input of higher $B_1$-field thus reducing scan time, or increase the signal-to-noise ratio without exceeding SAR limits.

The present invention contemplates an improved apparatus and method that overcomes the aforementioned limitations and others.

In accordance with one aspect of an embodiment of the invention an MRI apparatus is provided. The apparatus includes a main magnet for generating a main magnetic field in an examination region, a plurality of gradient coils for generating gradient fields within the main field, an RF transmit coil for transmitting RF signals into the examination region and exciting magnetic resonance in a subject disposed therein in accordance with a plurality of imaging parameters, the transmitted RF signals having a SAR associated therewith, and a SAR processor for maintaining the transmitted RF signals below a prescribed SAR level.

In accordance with a more limited aspect of an embodiment of the invention the SAR processor includes reference SAR data as a function of subject location.

In accordance with another aspect of an embodiment of the invention an MRI method is provided. The method includes the steps of generating reference SAR data as a function of subject position, selecting a subject position to image, generating a main magnetic field in an examination region, generating gradient fields within the main magnet, transmitting RF pulses into the examination region to excite magnetic resonance in a subject disposed therein, the RF pulses having SAR values associated therewith, and maintaining the SAR values below prescribed SAR limits in accordance with the reference SAR data at the selected position.

In accordance with another aspect of an embodiment of the invention an MRI apparatus is provided. The apparatus includes reference SAR means for generating reference SAR data as a function of subject position, main magnetic field means for generating a main magnetic field in an examination region, gradient means for generating gradient fields within the main magnet, RF transmit means for transmitting RF pulses into the examination region to excite magnetic resonance in a subject disposed therein, the RF pulses having SAR values associated therewith, and SAR adjusting means for maintaining the SAR values below prescribed SAR limits in accordance with the reference SAR data at the selected position.

One advantage of an embodiment of the invention is that it facilitates efficient use of the MR system.

Another advantage of an embodiment of the invention is that it provides SAR limits based on an anatomical model.

Another advantage of an embodiment of the invention is that it accounts for changes in SAR as a function of patient position.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 1:
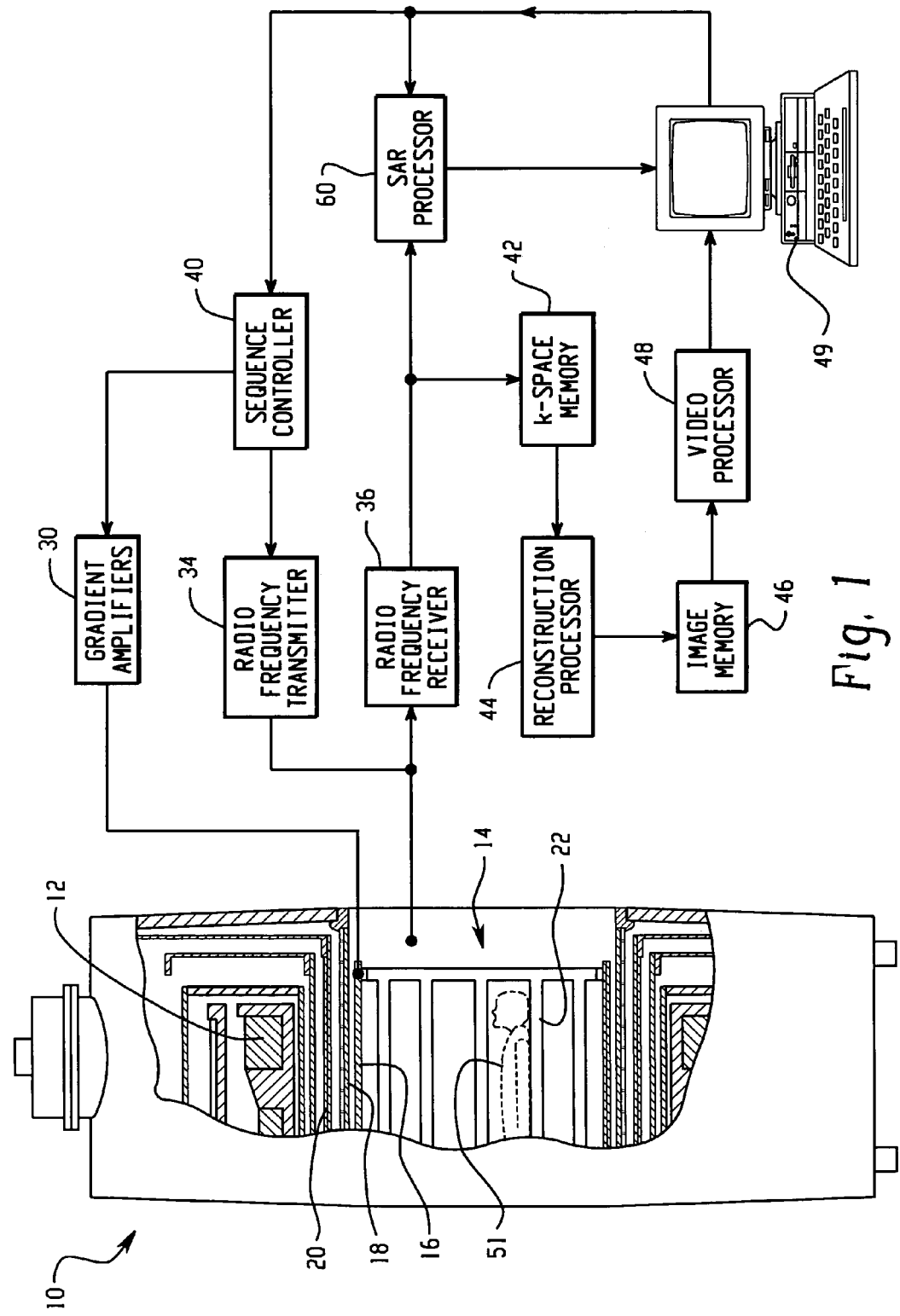
FIG. 1 shows a side view of a magnetic resonance imaging apparatus.

With reference to FIG. 1, a magnetic resonance imaging scanner 10 includes a cylindrical main magnet 12, which is preferably superconducting and cryoshielded. The main magnet 12, and the housing 13 in which it is disposed, defines a magnet bore 14, or examination region, inside of which a patient 51 or other imaging subject is placed for imaging. The main magnet 12 produces a spatially and temporally constant and uniform main magnetic field oriented along a longitudinal (z) axis of the bore 14. Instead of a superconducting magnet, a non-superconducting magnet can be used. Moreover, a vertical magnet, an open magnet, or other type of main magnet can be employed instead of the illustrated horizontal cylindrical main magnet 12.

The MRI apparatus also includes magnetic field gradient coils including a primary gradient coil 16 and optionally a shield gradient coil 18 that cooperatively produce magnetic field gradients in the bore 14 for spatially encoding magnetic resonance signals, for producing magnetization-spoiling field gradients, or the like. Preferably, the magnetic field gradient coils include coils configured to produce magnetic field gradients in three orthogonal directions including transverse x- and y-directions. In addition to the shield coil 18, an optional cold shield 20 provides a high conductivity eddy current surface for residual gradient fields thus protecting the magnet coils still further away.

A radio frequency coil assembly 22, for example a quadrature body coil, generates radio frequency pulses for exciting magnetic resonances. The radio frequency coil assembly 22 can also serve to detect magnetic resonance signals. Optionally, head coils or other local radio frequency coils (not shown) are included for exciting and/or detecting magnetic resonances at localized areas in the bore 14.

Gradient pulse amplifiers 30 deliver controlled electrical currents to the magnetic field gradient coils 16, 18 to produce selected magnetic field gradients. A radio frequency transmitter 34, preferably digital, applies radio frequency pulses or pulse packets to the radio frequency coil assembly 22 to generate selected magnetic resonance excitations. A radio frequency receiver 36 also coupled to the radio frequency coil assembly 22 receives magnetic resonance signals. If more than one radio frequency coil is provided (such as a local coil or phased coil array), then different coils are optionally used for the magnetic resonance excitation and detection operations.

A sequence controller 40 communicates with the gradient amplifiers 30 and the radio frequency transmitter 34 to produce selected transient or steady state magnetic resonance configurations in the subject, to spatially encode such magnetic resonances, to selectively spoil magnetic resonances, or otherwise generate selected magnetic resonance signals characteristic of the subject. The generated magnetic resonance signals are detected by the radio frequency receiver 36, and stored in a k-space memory 42. The imaging data is reconstructed by the reconstruction processor 44 to produce an image representation that is stored in an image memory 46. In one embodiment the reconstruction processor 44 performs an inverse Fourier transform reconstruction.

The resultant image representation is processed by a video processor 48 and can then be displayed on a user interface 49, which can be a personal computer, workstation, or other type of computer and can be stored thereon. The user interface 49 also allows an operator to communicate with the magnetic resonance sequence controller 40 to select magnetic resonance imaging sequences, modify imaging sequences, execute imaging sequences, and protocols and so forth.

In establishing the RF transmit parameters of the imaging sequence, it is desirable to make use of available RF transmit power while staying within prescribed SAR limits. In one embodiment of the invention, this is accomplished by adjusting the duty cycle of the RF transmit signals or the transmit signal B1 field strength according to a SAR model stored in a SAR processor 60.

In one embodiment, SAR values are determined in accordance with the following steps. First, a subject is placed in the examination region and a head-to-toe scout scan is performed at a SAR level that is known to be within SAR limits. For the purpose of the scout scan, a magnetic field gradient is established in the z-direction (i.e. along the longitudinal axis of the subject). Starting at the head, and at given increments (e.g. 10 cm), a series of RF signals are sent from the RF controller to the RF transmitter and associated RF pulses are transmitted into the examination region such that magnetic resonance is induced in a subject disposed therein.

Induced RF signals emanating from the examination region are detected by the RF receive coil. The signals are directed to the RF receiver 36 and are subsequently directed to the SAR processor 60. subject distribution processor 100 where the B1 flip angle associated therewith is determined.

In one embodiment, three equal pulses are transmitted in series and a ratio between resulting echo amplitudes received by the RF receive coil is used to determine the B1 flip angle associated with the power of the RF pulses.

Once the B1 flip angle has been calculated, the RF power associated with a given flip angle (e.g. ninety degrees) is determined. The process of performing a series of RF pulses, estimating the B1 flip angle, and calculating the RF power associated with a given B1 flip angle is carried out incrementally from head-to-toe. Accordingly, for the given flip angle, a plot of RF power necessary to achieve the given flip angle is obtained along the length (i.e. distal position) of the subject.

Figure 2:
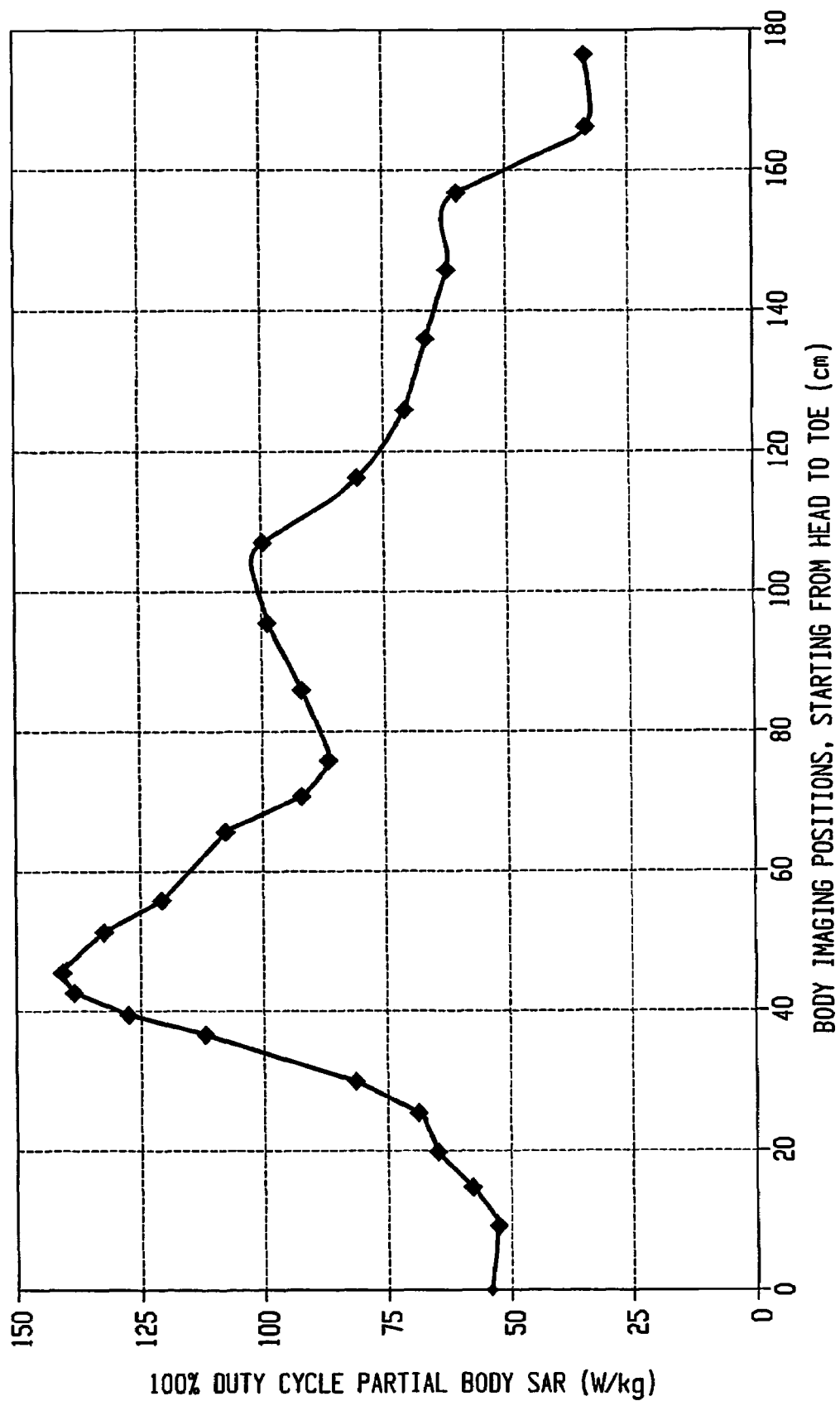
FIG. 2 shows reference SAR data.

Next, the desired subject position and RF power curve are directed to the SAR processor for calculating the duty cycle of the RF transmissions to be used during the imaging sequence. FIG. 2 shows reference values by which such a calculation is made.

Referring more specifically to FIG. 2, 100% duty cycle partial body SAR is shown as a function of body imaging position. The curve shown in the graph is the result of a mathematical model which calculates SAR as a function of body position for a given human subject.

By way of example, calculations of partial body SAR as a function of patient position for an adult male human body in a B0 field of 3.0 Telsa are performed to generate the model data. B1 is fixed at 13.5 microtesla and RF duty cycle is 100% for the purposes of the model.

Figure 3:
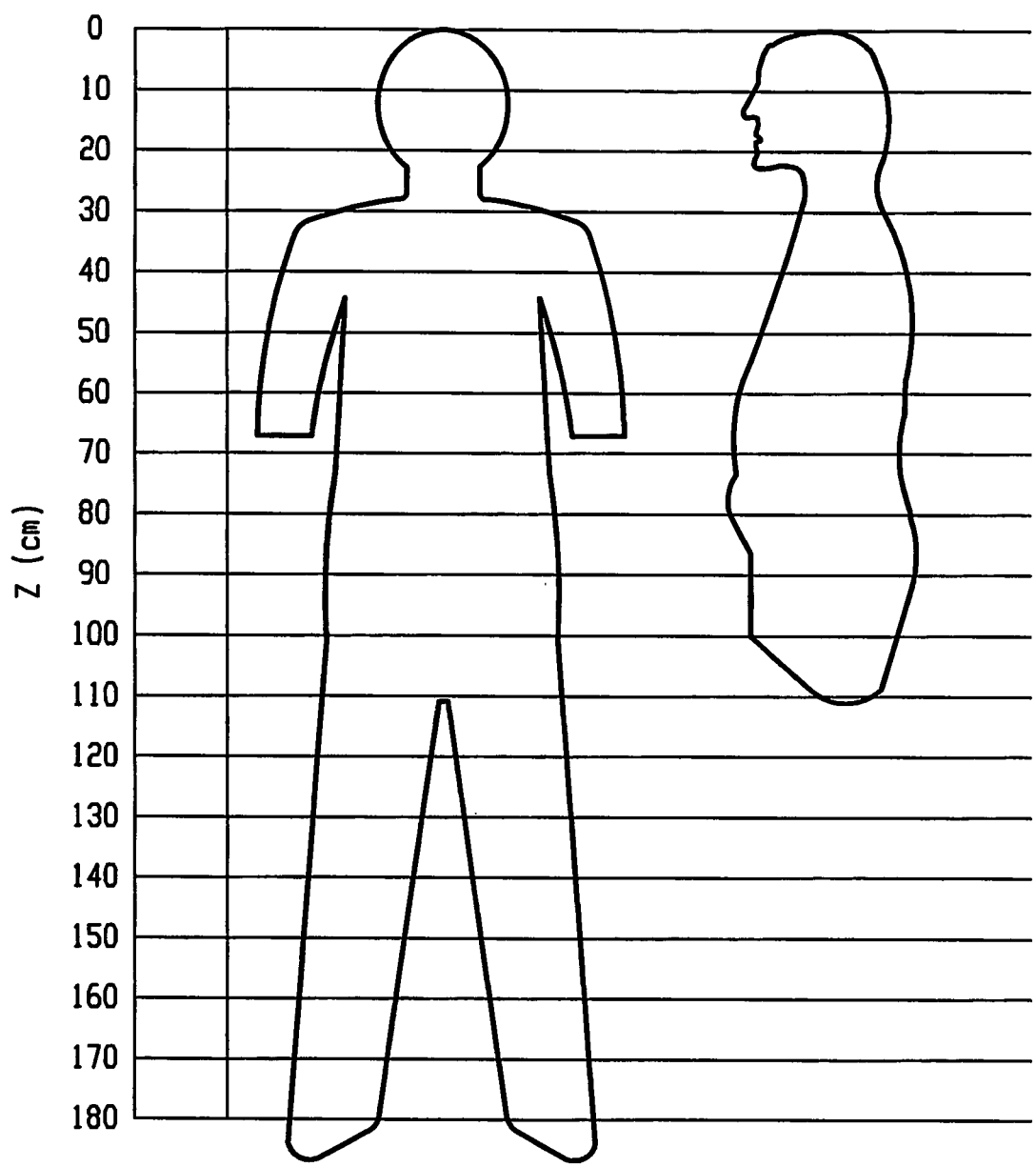
FIG. 3 shows characteristics of data input into a SAR model.

More specifically, the SAR calculations are made using a finite-difference time-domain (FDTD) model. A modified realistic human body model is used in the simulation. Portions of the two arms of the human body model are trimmed as shown in FIG. 3 in order to simulate a patient's position such that the arms are stretched down without contacting any part of the abdominal region.

Figure 4:
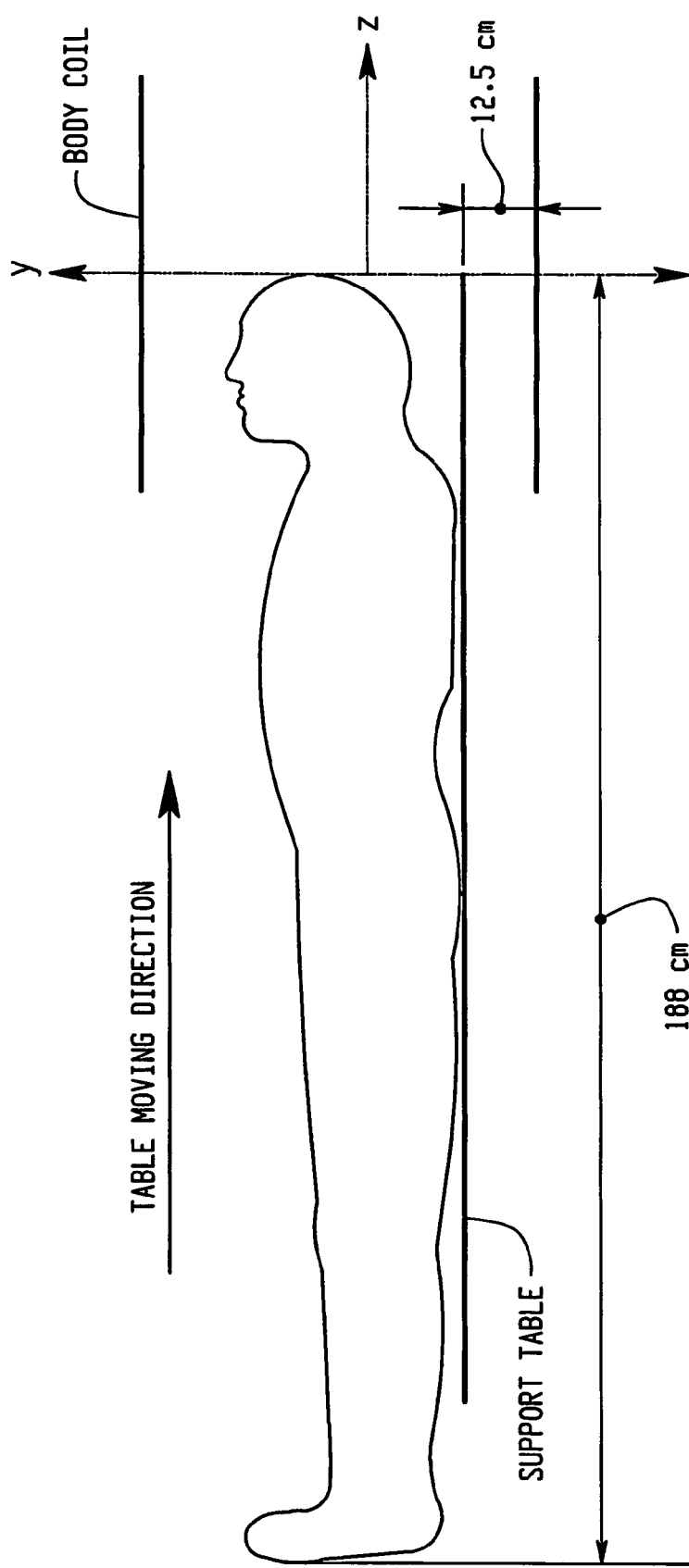
FIG. 4 shows subject positioning used for a SAR model.

As shown in FIG. 4, a human body model is placed inside a 3.0 T quadrature body coil (QBC) lying on a supporting table on y=−12.5 cm plane, or 12.5 cm below the isocenter of the body coil. The vertical position of the human body model relative to the body coil comes from considering that, the couch is 15 cm below the isocenter of the body coil and the thickness of a pad on the couch is 2.5 cm. In accordance with the model, the subject table moves in the z direction with z=0 at the isocenter of the body coil. Initially the top of the head is centered at the isocenter. As the human body model is moved into the body coil, z is the distance between the top of the head and the isocenter, as shown in the diagram of FIG. 3. $B_1$ and SAR are calculated in each z position until the ankle of the human body model is centered at the isocenter. For the modified human body model, it has the height of 1.88 m from top of the head to its toe with the maximum width of 57 cm from left arm to right arm. The mass of the human body model is 103 kg with total 805,495 FDTD cells. The same RF voltage sources are applied in all imaging positions.

The duty cycle of the RF transmissions to be used during the image acquisition protocol is determined by finding the SAR value in the model that corresponds to the position of the subject being imaged and adjusting the duty cycle of the RF transmissions accordingly. In other words, given a subject location of 40 cm, the model provides a partial body SAR value of approximately 25 W/kg. This value is used adjust the duty cycle of the RF transmissions so that the SAR during the imaging protocol falls within prescribed limits, yet makes use of available RF power.

In order to carry out the imaging process, the main magnetic field is then generated in the examination region via control of the main magnet. Magnetic field gradients are established in the examination region in, for example, slice, phase, and read encode directions using the gradient magnet system. In accordance with the calculations above, radio frequency pulses are transmitted into the examination region to excite resonance in the subject disposed in the examination region within SAR limits.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. An MRI apparatus comprising:
   a main magnet for generating a main magnetic field in an examination region;
   a plurality of gradient coils for generating gradient fields within the main field;
   an RF transmit coil for transmitting RF signals into the examination region and exciting magnetic resonance in a subject disposed therein in accordance with a plurality of imaging parameters, the transmitted RF signals having a SAR associated therewith; and
   a SAR processor for maintaining the transmitted RF signals below a prescribed SAR level,
   wherein the SAR processor includes reference SAR data as a function of subject location and the SAR data is derived from an FDTD model having human body data as input.

2. An MRI apparatus as set forth in claim 1 wherein the SAR processor maintains the transmitted RF signals by adjusting the RF duty cycle associated therewith.

3. An MRI method comprising the steps of:
   generating reference SAR data as a function of subject position;
   selecting a subject position to image;
   generating a main magnetic field in an examination region;
   generating gradient fields within the main magnet;
   transmitting RF pulses into the examination region to excite magnetic resonance in a subject disposed therein, the RF pulses having SAR values associated therewith; and
   maintaining the SAR values below prescribed SAR limits in accordance with the reference SAR data at the selected position,
   wherein the step of generating the reference SAR data includes modeling partial body SAR as a function of subject position using a FDTD model.

4. An MRI apparatus comprising:
   reference SAR means for generating reference SAR data as a function of subject position;
   main magnetic field means for generating a main magnetic field in an examination region;
   gradient means for generating gradient fields within the main magnet;
   RF transmit means for transmitting RF pulses into the examination region to excite magnetic resonance in a subject disposed therein, the RF pulses having SAR values associated therewith; and
   SAR adjusting means for maintaining the SAR values below prescribed SAR limits in accordance with the reference SAR data at the selected position,
   wherein the reference SAR means includes modeling partial body SAR as a function of subject position using a FDTD model.

* * * * *